United States Patent
Edwards et al.

(10) Patent No.: US 6,922,652 B2
(45) Date of Patent: Jul. 26, 2005

(54) AUTOMATED QUALITY ASSURANCE METHOD AND APPARATUS AND METHOD OF CONDUCTING BUSINESS

(76) Inventors: Jim Edwards, 107 Hilltop Dr., Jefferson, GA (US) 30549; Darren Wattles, 3840 Leach Rd., Gainsville, GA (US) 30506; Jim Tomlin, 819 W. Ridge Rd. SW., P.O. Box 908854, Gainsville, GA (US) 30501

( * ) Notice: Subject to any disclaimer, the term of this patent is extended or adjusted under 35 U.S.C. 154(b) by 0 days.

(21) Appl. No.: 10/667,154

(22) Filed: Sep. 19, 2003

(65) Prior Publication Data

US 2005/0075798 A1 Apr. 7, 2005

(51) Int. Cl.$^7$ .............................................. A01K 43/08
(52) U.S. Cl. ...................................................... 702/128
(58) Field of Search .................................. 702/128, 104; 426/74, 646, 59, 58, 84; 700/117; 250/559; 209/551, 511; 374/101; 219/391, 700

(56) References Cited

U.S. PATENT DOCUMENTS

| | | | |
|---|---|---|---|
| 4,106,340 A | * | 8/1978 | Hamid ........................ 374/101 |
| 5,357,441 A | * | 10/1994 | Petty et al. .................. 702/104 |
| 6,369,401 B1 | | 4/2002 | Lee |
| 2002/0014444 A1 | * | 2/2002 | Hebrank ...................... 209/511 |
| 2003/0024744 A1 | | 2/2003 | Ring |

FOREIGN PATENT DOCUMENTS

WO   PCT/6B99/00766   9/1999

OTHER PUBLICATIONS

Opton's 3D Moire Mea, 1982, opton.

* cited by examiner

*Primary Examiner*—John Barlow
*Assistant Examiner*—Tung Lau
(74) *Attorney, Agent, or Firm*—Newman & Newman LLP; John P. Luther

(57) ABSTRACT

The present invention provides a dynamic continuous and/or semi-continuous and/or static product measurement characterizing and identifying system and apparatus for food stuffs and food product portions and other objects comprising a conveyor means for transport of product or object to be measured to one or more detection regions to detect information comprising height, length, width, dimensional, spatial or topological characteristics, coloring characteristics, and/or moisture content and/or weight and temperature while conveyed products are in motion or static or a combination thereof on said conveying means.

25 Claims, 1 Drawing Sheet

AUTOMATED QUALITY ASSURANCE METHOD AND APPARATUS AND METHOD OF CONDUCTING BUSINESS

FIELD OF THE INVENTION

The present invention relates to a method and apparatus, and method of doing business thereby, for automating quality control functions in processed food production and preparation of beef, poultry and other food segments and portions, and more particularly to automated means and method for dimensional sizing, weighing and temperature testing and spatial characteristic determination of food and other products.

BACKGROUND OF THE INVENTION

To further efficiency in modem food product processing and packaging operations, and in food portion control, efforts have been made to replace formerly manually conducted operations with automated procedures and methods. Such methods and products are particularly desirable in quality assurance operations and procedures to ensure that regulated and mandated quality standards are consistently adhered to throughout production operations.

For example, in U.S. patent application publication No.: U.S. 2003/0024744 (Feb. 6, 2003) to Ring, there is disclosed a data acquisition and/or control method and device which employs a conveyor weigh scale, or "weigh scale control", which is said to automatically determine a crucial sample period for accurately weighing various food products. The described method also employs an algorithm for data acquisition and control in a food product weighing operation. In this method, a conveyor weigh scale senses a dynamic weight of a product as it passes over a weigh scale, which can be expressed as a weight waveform of sensed weight over time as the product passes over the scale. As described, an accurate weight reading for the moving product is made during a brief sample period within the waveform where weight readings are most constant and representative of the static weight of the product. This method is said to be an advantage over conventional continuously moving product scales which use laser sensor or photosensitive components, such as an optical or other external triggering device. These devices are used to detect the entry of a product into a weigh scale, and then actuate the scale which uses fixed timing numbers to estimate the position of the sample period on a weight waveform to make weight measurements.

The improvement associated with this method is said to be the provision of a software algorithm for a weight scale associated with a continuously moving conveyor which is capable of positioning the sample period on each product weight waveform and in which the weight and speed of the product passing over the scale does not affect the positioning of the sample period. The algorithm calculates the sample period using waveform slope characteristics.

The weight measurement method described above is also said to be useful with such conventional food processing methods, such as illustrated, for example, in U.S. Pat. Nos. 5,704,265; 5 and 5,724,874 which is a slicing machine with a conveyor drive/classifier system that is responsive to a weigh scale to direct products within a weight tolerance to an "accept conveyor, and out-of-weight tolerance products to a "reject" conveyor. The slicing machine produces a series of stacks of food loaf slices which move outwardly of the machine on an input conveyor which, as described, continuously senses the weight of the sliced product appearing on the scale, which, in turn, outputs a continuous succession of weight readings of samples at regular time intervals to define corresponding waveforms, and which are characterized as dynamic weight measures of product. The assemblage enables rapid weight measurement on the order of five-hundred samples per second, with a rapid conveyor product speed of over one-hundred product stacks per minute. The system is applicable to all different types of commercial food product loaves, such as ham, beef, pork, fish in a variety of shapes and sizes, and in differently shaped stacks of food product.

Other conventional food processing measurement systems include two-dimensional (2-D) imaging systems to determine length and width, and used, for example, in oyster measurements and in sizing other food objects. These systems typically produce a 2-D image which corresponds to an amount of light and corresponding current, which is picked up by pixels of a charge-coupled device (CCD) camera, and which is positioned to receive images from a particular area. These systems are also able to obtain individual weight data per product, such as the weight of an oyster, by correlating a sample group weight of food products with pixel data using an equation relating to 2-D image and volume.

Further refinements to such methods of determining food product volume employ three-dimensional (3-D) optical volume measurement such as disclosed in U.S. Pat. No. 6,369,401 to Lee. In this method, one or more lines of radiation are projected from a radiation source, such as a laser light source, onto a food object, and thereafter detecting lines of radiation reflected from the object. Reflected radiation is compared with that reflected from a reference surface to determine the height, length and width of an object at a location corresponding to at least one line of radiation impinging on the object. As further disclosed in this method, several laser lines are impinged onto a surface area on which a food product object is located, and onto a reference surface of which no food product object is located. A light sensitive device, such as a camera, having a plurality of pixel elements that can receive light from a plurality of surface locations, which is light reflected from the food product object, or surface, is used to determine light intensity received, and displacement of laser lines relative to a reference location.

Raw image data from the camera is received by a central processing unit (CPU), which determines the binary image of projected area to determine length and width dimensions. The CPU also uses laser line displacement data to determine object height at the various locations of the object, all of which data is then used by the CPU to calculate the product or object volume.

Another food product data processing/process control system and method is discloses in International Patent Application No. PCT/GB99/00766 to Whitehouse. In this system, a food product traverses an inspection region on a conveyor belt, and a transducer determines shape; size and cross-section of the product in the inspection region. Data generating transducers can be rotated about an object or product to be measured so as to inspect the whole of the product surface for accurate size and shape measurements, with signals generated when a length of product enters and leaves an inspection region, and with computation means capability to produce product arrival and product departure signals.

As also disclosed, data generating laser displacement transducers may be mounted in a ring pattern around or at an inspection site or region, and situated to direct their beams through a gap between two in-line conveyors, with the ring being driven by a servo motor, and with output data of the transducers logged by a computer means.

In yet another example of conventional product characteristic data gathering in commercial food processing techniques, U.S. Patent application publication No. U.S. 2002/0014444 (Feb. 7, 2002) to Hebrank describes a method and apparatus for automated poultry egg classification. A conveying system is used transport eggs to an inspection station where, among other characteristics, egg temperature is measured by a thermal codling system which measures temperature by detecting corresponding infrared radiation, thereby generating corresponding signals which are sent to a controller, or CPU.

Currently, in conventional poultry, meat and processed food plant operations in general, quality control and assurance techniques are oftentimes labor intensive. For example, in a typical poultry plant operation, a sample of all boneless breast meat product is tested for size, weight, temperature and other characteristics and/or defects or standard deviations by method(s) which require at least some aspect of manual labor or exertion to produce measurable data, e.g. a quality assurance data point. Usually, to obtain weight measurements, an employee is required to extract a sample of product from a product process line and place it on a scale for weighing. The product weight can then be recorded in a log, or other database, such as a computer database program.

Product thickness, or other dimensions of width and length, are also typically manually measured, such as, for example, by using calipers, which data is also manually logged, or otherwise fed to a database. The temperature of each product sample is also manually checked and recorded. Such labor intensive efforts are undesirable in that up to two minutes or more is required to check each product sample, thereby resulting in significantly less data generated than if performed by automatic machine means. Additionally, such human intervention with quality assurance checking procedures invariably results in inconsistent or even fabricated data generation leading to unnecessarily unreliable quality assurance measures.

It is therefore desirable, and an object of the present invention, to provide a completely automated method and system to generate all data contemplated as required for any food product processing quality assurance program or other product standardization or portion control operation.

SUMMARY OF THE INVENTION

In accordance with those objects and desires set forth above, the present invention provides a method and apparatus, and method of doing business thereby, of automating quality control and assurance in commercial food processing, packaging and handling. In this inventive product measuring system total product/object measurement, e.g. length, width, height, weight, spatial characteristics volume and temperature measurement functions and other product/object characteristic determinations, are combined in an automated means, in which one or more sample food products on an automated conveying means is transported to one or a plurality of inspection sites or regions, which can be located in a housing means. In accordance with this invention, once transported to the desired location(s), a product sample may traverse one or more inspection regions, wherein it is preferred that out of a plurality of possible inspection means at least one detection means is provided which is effective to measure product dimensions and spatial characteristics, e.g., the height, length and width, volume and generally the 3-D topography and the unique spatial characteristics of a sample product; another detection means measure is provided to measure the weight of said sample product; and an additional detection means is present to measure the temperature of the sample product. Multiple detection means are contemplated for use in a variety of embodiments of this invention to measure and/or detect any desired characteristic of a food product or any object traversing an inspection region. The system can also be optionally provided with accept output conveyor means and reject output conveyor means, for example, for defective products, or products falling outside of standardization parameters, as desired. The inventive system is also contemplated for use with one or more executable programs to generate, process and store data in a database and to operate all contemplated functions of the invention, bar code generating means to codify product measurement characteristics and any other conventional data processing technology.

The present invention as to its manner of operation and further objects and advantages is best understood by reference to the following Detailed Description of Preferred Embodiments, accompanied by reference to the drawing.

DETAILED DESCRIPTION OF PREFERRED EMBODIMENTS OF THE PRESENT INVENTION

Figure 1:
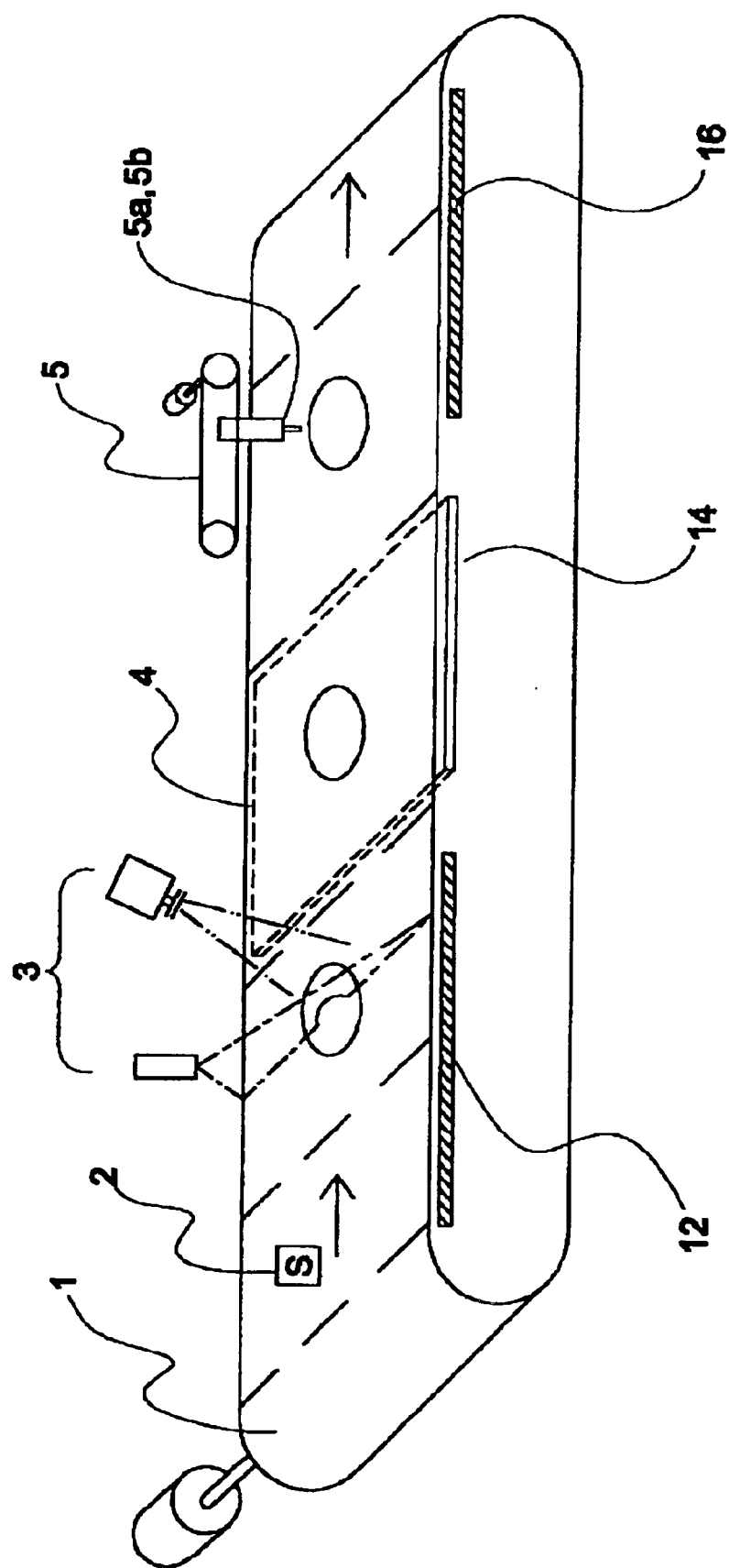
FIG. 1 is a perspective schematic view of an embodiment of the inventive measuring method and system for automated dynamic product configuration/dimensional determination, weight and temperature determination.

The present invention provides an automated food product and object measuring system which is particularly suited for use in food plant product quality assurance and control operations. In this invention, a conveyor means, such as a servo-computer operated conveyor belt, transports one or more, or a plurality of products, to one or more inspection or measurement regions to be measured for, e.g. quality control purposes, product standardization and packaging, or for any reason contemplated. The product may be a poultry part or food portion, such as a boneless chicken breast, or a beef or pork section or portion, a whole fish, or any food or prepared food product contemplated, such as chicken or beef pies, prepared casseroles and the like, or any non-food product desired for characteristics measurement and/or identification.

In this exemplified embodiment, once entering an inspection region by way of conveyor means, the product is subjected to a first detection means for dimensional or spatial dimensional or otherwise total topological and/or 2-D or 3-D detection and determination including, for example, the product's height, length and width, and spatial and/or topological characteristics; a second detection means for product weight determination; and then a third detection means for product temperature determination, all of which collected information can be automatically stored in a database. The order of placement of detection means can be that of any order as desired and is not critical to the practice of this invention. However, in a preferred embodiment, there is thought to be an advantage to conducting a spatial or topological determination prior to a temperature determination, as the temperature of an object can then be measured at an optimum local of an object, for example, the thickest portion of an object as desired. The inventive measuring system provides for an efficient, humanintervention-free and accurate snapshot product review at any point desired in a food product production line, with a concomitant reduction in labor required for its undertaking, and an elimination of a specially trained labor force required for product quality control and assurance operations. The inventive system by way of its conveyed continuous operation also enables a significant increase over conventional manual operations in product sample(s) review and quality control data collection.

Turning now to FIG. 1, there is shown a perspective schematic view of a preferred embodiment of the inventive product sample measuring/quantifying system for automated dynamic product configuration/dimensional determination, weight and temperature determination. In FIG. 1, a conveyor means 1, such as a standard conveyor belt, transports one or more, or a plurality, of food product samples 2, such as a poultry portion or beef or pork food portion for human, and/or animal consumption, to one or more inspection regions. An operator can manually place a food product 2 on the conveyor means 1, or it may be deposited from a hopper means (not shown) or by any suitable conventional deposit means desired or contemplated. The speed of conveyor means 1 can be set and controlled by a computer means (not shown) or other Central Processing Unit (CPU), with stop/start and food product entry and depart functions automated and controlled as well by the computer means or CPU, or other control function means.

Upon being conveyed to a first inspection region 12, a first detection means 3 is similarly situated and is effective to detect and make 3-D measurements and/or determine product configuration of the sample product. First detection means 3 can be any known or conventional device, preferably such as a scanning device, for example, a laser scan, to determine the height, length and width of the sample product at any cross-sectional plane of the product to provide an accurate spatial, topological, two- or three-dimensional product configuration output profile and volume of the product. Irregularly shaped food products such as boneless chicken parts have a varying topography and are preferably checked and measured for total length, mean and average height and width through several cross sectional portions or preforms of the sample. If preferred, two-dimensional measurements are also contemplated.

Scanners contemplated as useful in this example as a first detection means, and in this invention in general, can be any conventionally available technology, such as, for example, two and three-dimensional optical sizing systems employing camera means positioned in inspection region 12 to receive images from the inspection region. Such devices are well known, of which examples are discussed in U.S. Pat. No. 6,369,401, the disclosure of which is incorporated herein by reference. Another example of conventional 2-D or 3-D spatial imaging methodology or technology useful herein includes that disclosed in the Opton non-contact whole field 3-D Moire measurement machine series, such as first described in Takeda, "Fourier Transform profilometry for the automatic measurement of 3-D object shapes", University of Electrocommunications (1982), all of which is incorporated by reference herein. In this system an optical sensor head which acquires images is provided, and which are based on 3-D calculations. In operation, a grating pattern is projected onto an object to be topologically characterized from a grating projector by way of a strobe means, e.g., a Xenon strobe, with deformed grating patterns of the surface of the object to be measured by being picked up and entered into a computer by way of detection from a change-coupled device (CCD) camera which digitizes the grating images and general B/W images on the object. As is known a CCD camera contains light sensitive integrated circuits which store and display the data for an image in such a way that each picture element (pixel) in the image is converted into an electrical charge of which its intensity is related to a color of the color spectrum. For example, in a system supporting 65,535 colors, there will be a separate value for each color that can be stored and recovered. This method and system is known for its improved shutter speed and effectiveness in imaging and use with moving objects to produce accurate shape and color measurements with wide field, high resolution and high speed measurements via the use of high speed, strobe aided cameras. The system is also equipped with a laser pointer for auto-focusing and controlling the orientation of the camera, a lighting means, e.g. a white light lamp to illuminate an object targeted for measurement and for illuminating ink lines and reference marks as desired. An optical probe means for uniaxial point measurement, or a snap-shot one point 3-D measurement, at any point desired in an object is another feature. As also discussed, a grating shifting mechanism can be employed to improve data spatial resolution.

As mentioned, in operation a grating pattern is projected onto a surface to be measured which is deformed according to an object's particular topography. The deformed grating pattern taken into a computer by the CCD camera is saved as a digital image. With a flat surface to be measured located at a reference position, for example, the most desirable focus position, the deformed image received by the camera will be one of substantially straight lines which may have a particular pitch characteristic. For a non-flat surface at a reference position to be measured, the deformed image received by the camera will be one of non-straight lines and a changed grating pitch, with a change of light intensity of the grating image, which is measured and processed. Thus, for example, the first image of a flat or substantially flat object, such as a conveyor belt surface, is used a reference wave with a certain frequency in comparison with a second image of a deformed wave with its phase modulated. The phase difference can then be calculated, for example, by use of an algorithm, such as the Moire 3-D algorithm as based on the Takeda publication, between the reference and deformed waves for individual pixels of the CCD camera, with a depth (Z coordinate) and X and Y coordinates obtained. Many other 2-D or 3-D imaging/topological measuring methods and systems are known, any of which are contemplated for use herein.

By way of a series of snap shots of cross-sectional segments of a sample product, providing height, length and width data of a varying topography of a products' configuration, the product's volume may be determined, as well as its spatial characteristics, such a detailed topographic map, from which a host of desired information can be extracted, including, for example, maximum thickness and length along any axis of interest. Other information operations which might be performed include, for example, product outline template checking, shape irregularity measurement such as for unusual protuberances, shape checking, and thinness and thickness checking over selected areas, all of which can be automatically calculated and determined by computer means or a CPU station. As can be seen, an enormous amount of reliable data, and sample product information, can be gathered and logged or processed in a rapid amount of time to control product output quality as precisely as desired or required.

Further proceeding into another inspection region, inspection region 14 in FIG. 1, by means of conveyor means 1, product sample 2 is next subjected to a weight detection or determination means 4 which is effective to determine total product sample weight. Weight detection means 4 situated in inspection region 14 can be of any known conventional technology, such as a load cell or other device effective for dynamic weight measurement of products on a continuously moving weigh conveyor. Examples of such conventional continuous weighing technology suitable for use in the present invention are provided, for example, in U.S. Patent Application Publication No. U.S. 2003/0024744. Any of the many conventional load cell weighing systems or indicators are suitable for use in this invention, including, for example, that provided by Weigh-Tronix, for weighing mixed items of varying size and weight, i.e. irregularly shaped and configured food product samples, in high speed conveyed weight validation. Other preferred suitable examples useful herein include such load cell-based process weighing systems as provided by BLH Vishay weight indicators and products, and that of Sensortronics and RL Scales, Inc., which provide load cell weighing systems for use in automatic check out counters, as well as in picking/shipping systems and general industrial applications, any of which such conventional weighing technology is contemplated for use in this invention.

Having undergone dimensional/spatial/topological configuration, volume and weight analysis, product samples next are transported in FIG. 1 by conveyor means 1 into a third inspection region 16 for temperature determination/analysis or temperature verification. As shown in FIG. 1, a temperature detection means 5 is situated in or contemporaneous to inspection region 16, and is effective for continuous dynamic temperature measurement of food product samples continuously traversing region 16. In this preferred embodiment, a temperature prove means 5a, 5b is indicated for use, which may be a computer engaged probe insertable in any cross sectional portion of a sample product, such as one of irregular topographical product configuration, to provide an average or mean temperature per piece or product sample, and to ensure accurate temperature measurement. As is known, dwell times of such temperature measurement products can be set as desired to further ensure accurate product temperature measurement on a continuously moving conveyed sample production line.

Also suitable for use in this invention are non-contact temperature measurement devices, such as radiation thermo-detection means which are capable of providing accurate and reliable temperature determinations and values at a distance over a continuously moving conveyed line. Such instruments, as known, employ optical components which can focus infrared radiation onto a solid-state detection where it is converted into an electrical signal and read out as temperature on a digital display. Some commercial examples include, for example, equipment produced by Raytek as the Thermalert series of products.

The conveying means of the invention can be any movable belt or moving surface means composed of, for example, antibacterial materials to avoid food product contamination, and can be actuated and speed controlled by a servo or computer means. The conveyor means in accordance with the invention may be continuously conveyed in product measurement operation, or, for example, stopped, started, or moved or pulsed at intermittent speeds, depending on the measuring or detection operation desired or contemplated, the desired speed of data generation, or any other production or business reason contemplated. The conveyor means is also preferably constructed of materials conducive and complimentary to detection measurement, such as light pulsed measurement and the like of product sample characteristics and with surface reference characteristics stored in a database in a computer means. It is also contemplated that the system be equipped with one or more conveying means for accepted sample products and for rejected sample products, with rejected samples being diverted to a conveyor or area by an acuateable component or means, such as a pop-up roller or automatically insertable panel or gate means, or other directing member means. The conveyor means can extend through one or more detection regions in a perpendicular or angled fashion, and be of a substantially flat surface or concave or convex in portions depending upon such factors as, for example, detection means employed, physical characteristics of a sample being measured, and the shape of a sample product to be measured.

Any conventional detection means is contemplated for use in the present invention, and which can be placed in any order in conjunction with the conveyer means. For example, in some food dye colored products, a color detection means may be desired, or in other applications useful to grade fish species via their natural color characteristics such as salmon, or beef sources or to detect blood spots in poultry and fish. Beef marbling may be detected in such a continuous operation to grade certain cuts, or to determine fat percentage in ground beef. Moisture content detection means may be employed, for example, along with weight and temperature measurements to gauge product shrinkage in processing and packaging operations.

Further, all of the data generated may be used in conjunction with bar code, or other coding technology, to grade specific or desired food lots and quantities, and/or used in conjunction with a user's computer network to receive product parameters, such as QA data, to report product line status to a control computer and to proved real time product reports.

In another aspect and embodiment of the present invention, it is further contemplated that the automated quality assurance method and apparatus my be employed in conjunction with one or more business methods, particularly methods of conducting food production operations, and stand alone quality assurance business method applications.

It will further be appreciated by those persons skilled in the art that the embodiments described herein are merely exemplary of the principles of the invention, and that many modifications and variations are possible without departing from the spirit and scope of the invention and claims.

We claim:

1. A dynamic continuous and/or semi-continuous or static product measurement, characterizing and identifying system for food stuffs and food product portions and other objects comprising a conveyor means for transport of product or object to be measured to more than one or a plurality of detection regions to detect information selected from height, length, width, dimensional spatial or topological characteristics, coloring characteristics, density characteristics, moisture content, weight and temperature while conveyed products are in motion or static or a combination thereof on said conveying means.

2. The system of claim 1, when employed to measure rigid bulk food.

3. The system of claim 1, wherein there are one or more discontinuities in the conveyor means.

4. The system of claim 1, wherein the conveyor means extends through more than one or a plurality of detection regions in one or more planes perpendicular or angled thereto, and further comprising computer means inclusive of data descriptive of the surface of the conveyor means where it extends through detection regions.

5. The system of claim 4 wherein the conveyor means is of a surface shape selected from the group consisting of substantially flat, concave in portions and convex in portions.

6. The system of claim 5 wherein the surface characteristics of the conveyor means form a reference database stored in a computer means to be compared to a transported sample product or product to be measured in one or more detection means.

7. The system of claim 1 further comprising reject product conveyor means and accepts product conveyor means.

8. The system of claim 1, further comprising one or more 2-D or 3-D dimensional and/or spatial characteristic measuring means effective to determine the length, width and height of an object and/or spatial or topological characteristics of an object.

9. The 2-D or 3-D measuring means of claim 8, which is an optical scanning measuring device.

10. The system of claim 1 further comprising a sample weight determining means.

11. The system of any of claim 8 or 12 wherein said dimensional/spatial measuring means and heat detection means is locatable in ring means surrounding said conveying means and rotatable to any desired angle to said conveying means while detecting product dimensions/spatial characteristics and temperature.

12. The system of claim 1, further comprising a contact or non-contact heat or temperature sample detection means.

13. Apparatus for a dynamic continuous and/or semi-continuous or static measurement, characterizing and identifying system for food stuffs and food product portions and other objects comprising a conveyor means for transport of product or object to be measured to more than one or a plurality of detection regions to detect information selected from height, length, width, dimensional spatial or topological characteristics, coloring characteristics, moisture content, weight, temperature and density while conveyed products are in motion or static or a combination thereof on said conveying means.

14. The apparatus of claim 13 further comprising a use to measure rigid bulk food.

15. The apparatus of claim 13 where there are one or more discontinuities in the conveyor means.

16. The apparatus of claim 13 wherein the conveyor means extends through more than one or a plurality of detection regions in one or more planes perpendicular or angled thereto, and further comprising computer means inclusive of data descriptive of the surface of the conveyor means where it extends through one or more detection regions.

17. The apparatus of claim 16 wherein the conveyor means is of a surface shape selected from the group consisting of substantially flat, concave in portions and convex in portions.

18. The apparatus of claim 16 wherein the surface characteristics of the conveyor means form a reference database stored in a computer means to be compared to a transported sample product to be measured in one or more detection means.

19. The apparatus of claim 13 further comprising reject product conveyor means and accept product conveyor means.

20. The apparatus of claim 13 further comprising one or more 2-D or 3-D dimensional and/or spatial characteristics measuring means effective to determine the length, width and height of an object and/or spatial or topological characteristics of an object.

21. The 2-D or 3-D measuring means of claim 20 which is an optical scanning/measuring device.

22. The apparatus of claim 13 further comprising a sample weight determining means.

23. The apparatus of claim 13 further comprising a contact or non-contact heat sample detection means.

24. The apparatus of claim 13 or 23 wherein said dimensional/spatial measuring means and heat detection means is locatable in a ring means surrounding said conveying means and rotatable to any desired angle to said conveying means while detecting product dimensions/spatial characteristics and temperature.

25. A method of conducting business comprising a dynamic continuous and/or semi-continuous product measurement, characterizing and identifying system and/or apparatus for food stuffs and food product portions and other objects comprising a conveyor means for transport of product or object to be measured to more than one or a plurality of detection regions to detect information selected from height, length, width, dimensional spatial or topological characteristics, coloring characteristics, moisture content, weight, temperature and density while conveyed products are in motion, static or a combination thereof on said conveying means.

* * * * *

(12) EX PARTE REEXAMINATION CERTIFICATE (6780th)
United States Patent
Edwards et al.

(10) Number: US 6,922,652 C1
(45) Certificate Issued: Apr. 21, 2009

(54) AUTOMATED QUALITY ASSURANCE METHOD AND APPARATUS AND METHOD OF CONDUCTING BUSINESS

(75) Inventors: Jim Edwards, Jefferson, GA (US);
Darren Wattles, Gainsville, GA (US);
Jim Tomlin, Gainsville, GA (US)

(73) Assignee: Processing Equipment Solutions, Inc., Gainsville, GA (US)

Reexamination Request:
No. 90/008,479, Mar. 5, 2007

Reexamination Certificate for:
Patent No.: 6,922,652
Issued: Jul. 26, 2005
Appl. No.: 10/667,154
Filed: Sep. 19, 2003

(51) Int. Cl.
*A01K 43/00* (2006.01)
*A01K 43/08* (2006.01)
*G06F 19/00* (2006.01)
*G06F 15/00* (2006.01)

(52) U.S. Cl. .................................................. 702/128
(58) Field of Classification Search .................. None
See application file for complete search history.

(56) References Cited

U.S. PATENT DOCUMENTS

| | | |
|---|---|---|
| 5,668,634 A | 9/1997 | Newman |
| 5,724,874 A | 3/1998 | Lindee et al. |
| 5,937,080 A | 8/1999 | Vogeley, Jr. et al. |
| 6,164,174 A | 12/2000 | Sigurdsson et al. |
| 6,826,989 B1 | 12/2004 | Wattles et al. |
| 6,866,417 B2 | 3/2005 | Gunawardena et al. |
| 2001/0032807 A1 | 10/2001 | Powell, Jr. |
| 2002/0014444 A1 | 2/2002 | Hebrank |

FOREIGN PATENT DOCUMENTS

| | | |
|---|---|---|
| WO | 99/47885 | 9/1999 |
| WO | 02/061368 | 8/2002 |

OTHER PUBLICATIONS

The DSI Horizon Customer Services Newsletter—Issue 4, Summer 1996. (Attached as Exhibit A to Gaydos Declaration—Exhibit 4 to Request for Reexamination).

Design Systems Incorporated Basic Training—Portioner™ 600 Series (Attached as Exhibit B to Gaydos Declaration—Exhibit 4 to Request for Reexamination).

*Primary Examiner*—Woo H Choi

(57) ABSTRACT

The present invention provides a dynamic continuous and/or semi-continuous and/or static product measurement characterizing and identifying system and apparatus for food stuffs and food product portions and other objects comprising a conveyor means for transport of product or object to be measured to one or more detection regions to detect information comprising height, length, width, dimensional, spatial or topological characteristics, coloring characteristics, and/or moisture content and/or weight and temperature while conveyed products are in motion or static or a combination thereof on said conveying means.

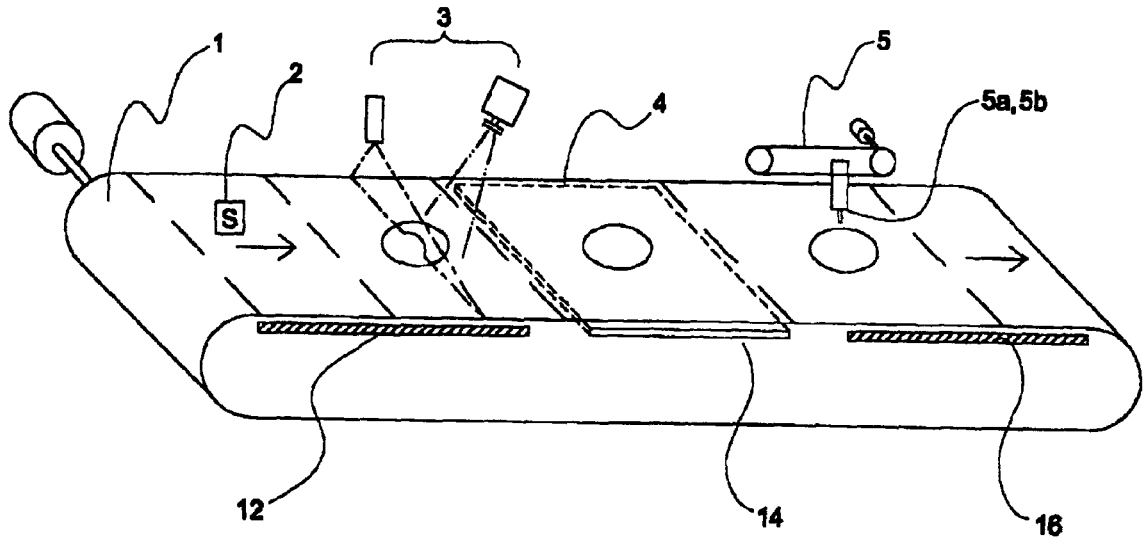

EX PARTE REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

Claims 1–25 are cancelled.

* * * * *